United States Patent
Haar et al.

(10) Patent No.: US 7,771,367 B2
(45) Date of Patent: Aug. 10, 2010

(54) LANCET WHEEL

(75) Inventors: Hans-Peter Haar, Wiesloch (DE);
Hans-Juergen Kuhr, Mannheim (DE);
Ortrud Quarder, Heidelberg (DE);
Joachim Hoenes, Zwingenberg (DE);
Dirk Voelkel, Weinheim (DE); Volker Zimmer, Laumersheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/779,070

(22) Filed: Jul. 17, 2007

(65) Prior Publication Data

US 2008/0021346 A1  Jan. 24, 2008

(30) Foreign Application Priority Data

Jul. 18, 2006  (DE) ................................ 06014898

(51) Int. Cl.
*A61B 5/157* (2006.01)
(52) U.S. Cl. ....................................... 600/583; 606/181
(58) Field of Classification Search ......... 606/181–183; 600/583, 584
See application file for complete search history.

(56) References Cited

U.S. PATENT DOCUMENTS

| | | | | |
|---|---|---|---|---|
| 6,706,159 B2 * | 3/2004 | Moerman et al. | ...... | 204/403.03 |
| 2003/0028125 A1 * | 2/2003 | Yuzhakov et al. | ........... | 600/583 |
| 2004/0039303 A1 * | 2/2004 | Wurster et al. | .............. | 600/584 |
| 2004/0059365 A1 * | 3/2004 | Abulhaj et al. | .............. | 606/181 |
| 2004/0230216 A1 * | 11/2004 | Levaughn et al. | ........... | 606/181 |
| 2006/0052810 A1 * | 3/2006 | Freeman et al. | ............. | 606/181 |
| 2006/0167382 A1 * | 7/2006 | Deshmukh | ................... | 600/583 |
| 2006/0184065 A1 * | 8/2006 | Deshmukh et al. | .......... | 600/583 |
| 2006/0241666 A1 * | 10/2006 | Briggs et al. | ................. | 606/181 |
| 2007/0016103 A1 * | 1/2007 | Calasso et al. | .............. | 600/583 |

FOREIGN PATENT DOCUMENTS

WO  WO 2005084530 A2 *  9/2005

* cited by examiner

*Primary Examiner*—Max Hindenburg
*Assistant Examiner*—Michael C Stout
(74) *Attorney, Agent, or Firm*—Baker & Daniels LLP

(57) ABSTRACT

A system for analyzing a bodily fluid is described, which contains at least one lancing element, such as a lancet, stored in a first magazine, and at least one test element with a detection area, stored in a second magazine, the detection area containing reagents if necessary for use in detecting the analyte. The system also includes a housing, which encloses at least part of the first magazine and the second magazine and includes an opening for placement of a body part. At least one of the lancing elements and at least one of the test elements are located below the opening, and one of the magazines is located at least partly between the opening and the other magazine. The two magazines may at least partially overlap. The lancing element and the test element may be moved toward the opening so the body part resting on the opening can be lanced with the lancing element and the emerging bodily fluid can be collected using the test element at the same opening.

24 Claims, 2 Drawing Sheets

LANCET WHEEL

BACKGROUND OF THE INVENTION

RELATED APPLICATIONS

This application is related to European Application Serial No. 06014898.8, filed Jul. 18, 2006, the disclosures of which are expressly incorporated by reference herein.

1. Field of the Invention

The present invention relates to the field of lancing devices for diagnostically determining blood parameters.

Collecting and analyzing bodily fluids takes place in many fields of medical diagnostics. It is therefore desirable to also enable routine tests to be performed quickly and reproducibly outside of the laboratory. Testing can be carried out with various bodily fluids, such as blood and/or interstitial fluid. These fluids can be tested with regard for various characteristics. The results of this test are important so that reliable diagnoses, therapeutic measures, and therapeutic monitoring can be carried out.

2. Description of the Prior Art

Single-handed blood glucose determination, known as home monitoring, is a method used around the world for monitoring diabetes. Blood glucose meters per the related art, such as the Accu-Chek® Sensor from Roche Diagnostics, are composed of a meter, into which a test element such as a test strip or sensor, for example is inserted. The test strip is brought in contact with a drop of blood that was obtained from the fingertip or another body part using a lancing device. The numerous system components such as a lancet, lancing device, test strip, and meter, for example require a great deal of space, and their handling is relatively complex. In the meantime, systems have also been introduced that have a larger number of integrated functions and, therefore, simpler handling. They include, e.g., the Accu-Chek® Compact from Roche Diagnostics, the Glucometer Dex from Bayer Diagnostics, and the Soft-Sense from Medisense. With the first two systems named, the test strips are stored in the meter and are presented for the test.

A next step forward in terms of compactness will involve selecting the geometry of lancing elements and analytical aids, such as disposables for example. Operation can be greatly simplified, for example, by providing a suitable combination of lancing procedure and sensor-based detection of analyte concentration on a test strip. The following represent examples of the related art.

An integrated system is described in patent application U.S. 2004/0039303A1 in which several test elements and several lancing elements are stored in a single device. The body part to be lanced is positioned on an opening of the device, through which lancing is carried out and through which fluid is obtained. The lancing elements and test elements are located in an integrated disposable below the opening. Due to this design, the lancing element must pierce the test element, so that the test element can absorb fluid directly from the puncture site. A disadvantage of the piercing of the test element is the potential that material will enter the body. In addition, after the test element is pierced, it has a potential point of leakage, through which fluid can enter the system and contaminate it. In addition, the needle can become dulled when it pierces the test element and thereby cause more pain.

Publication DE 10208575 describes an integrated blood analysis device which includes several lancing elements and several test elements. The test elements and lancing elements are mounted in a circular formation on two carriers, which are located one over the other. The lancing elements and test elements are brought into two different working positions; as a result, the user must use a different opening for lancing than for blood transfer. This system has the disadvantage that the patient must change the position of the body part to be lanced, thereby risking contamination of the housing and the surroundings with blood. When changing position, it is also necessary to position the lanced body part on the second opening exactly, to apply enough blood to the test element. Given that the lancing element and test element are in different positions, it may also be necessary to provide a separate drive for both elements.

The present invention relates to a system for analyzing a bodily fluid. The system may include at least one lancing element, which is stored in a first magazine, at least one test element, which is stored in a second magazine, a housing, which encloses at least part of the first magazine and the second magazine, and an opening for placement of a body part. In embodiments of the invention, at least one region of the first magazine and at least one region of the second magazine are located underneath the opening in the housing, and at least part of one of the magazines is located between the opening and the other magazine. In embodiments of the invention, the two magazines overlap at least partially underneath the opening.

The system may therefore include a housing with an opening. According to embodiments of the present invention, the lancing element and the test element may be moved toward this opening. As a result, it is made possible to perform the lancing procedure and draw up the fluid using the test element through a single opening. At least one recess in at least one magazine makes it possible to move an element of the magazine facing away from the opening through the plane of the other magazine, even though the two magazines are located underneath the opening such that they partially overlap. It is therefore made possible to lance the body part resting on the opening and draw up the emerging bodily fluid using the test element at the same opening, without having to guide or pierce an element of one magazine with an element of the other magazine. Since the magazines are located underneath the opening such that they partly overlap, one of the magazines is located between the opening and the other magazine. This magazine, which is located between the opening and the other magazine, may be referred to below as the "middle" magazine, and the other magazine may be referred to as the "lower" magazine. Either the first magazine, with the lancing elements, or the second magazine, with the test elements, may be positioned as the lower or middle magazine.

The recess formed at least in the middle magazine makes it possible to guide an element of the lower magazine through the plane of the middle magazine, without guiding the element through a part of an element of the other magazine. The recess can be moved underneath the opening by moving the magazine in the same manner as the indexing procedure. The recess in the one magazine should be so large that an element of the other magazine can be guided through the recess. The recess may also be larger, however. Parts of the magazines can be in contact with each other during the puncture procedure and/or drawing-up of fluid. This contact should not impair the motion of the element such that the functionality of the element is impaired, however. No additional movement of the magazine is required for this procedure. This means that no additional drive units are required to position the magazines beneath the opening.

The fact that the elements of the two magazines are not guided through the material of the other magazine during use generally prevents the material from one element from transferring to the other. As a result, the body part to be lanced is not contaminated by material from the pierced element, which can take place in the related art when the lancing element pierces the test element. In addition, the user does not need to move the lanced body part away from the opening for the lancing procedure and to apply fluid to the test element. As a result, the risk of contaminating the device with bodily fluid is reduced.

Furthermore, in embodiments of the invention, the two magazines can overlap completely. Lancing elements and test elements are positioned concentrically in this case. In the depicted embodiment of the invention, the magazines can be advantageously indexed further using just one drive. Suitable drives are known with clocks, for example. Despite the fact that there is just one drive, the magazines can be moved independently of each other. A recess may be located between each element in the middle magazine. By using only one drive, it is possible to match the motion of the two magazines with each other nearly exactly. Accordingly, the two magazines can be moved synchronously. The element of the other magazine can be used without restriction through this at least one recess. When the system is used, the recess can be moved underneath the opening by the same mechanism as is used to index the magazine.

In further embodiments of the invention, both magazines have a recess which alternates with the elements. In this manner, the elements of one magazine are located such that they alternate with the elements of the other magazine, so that, by simultaneously indexing the two magazines, one element can be presented for use under the opening. The magazines can be positioned relative to each other in a highly space-saving manner, while still ensuring that the lancing and test elements can be used through an opening. The handling of an integrated system of this type is very easy, since the user places his body part to be lanced on the opening and, subsequently, the puncture procedure and the test procedure can take place without any additional handling steps. Despite the compact design of the magazines, because of the separate storage of lancing elements and test elements, the lancing elements can be manufactured independently of the test elements. In this manner, the sterilization process, which is required for the lancing elements, can also be carried out separately from the test elements. The magazines can therefore be handled entirely separately from each other before they are used in the system, then they can be used together or separately in the system for the first time after manufacture or when they are used.

In embodiments of the invention, the structure that holds the lancing elements and test elements can be, e.g., a housing, in which several elements are stored separately from each other, as is the case, e.g., in a stacked housing design. As an alternative, the holding structure can be a main body, on which the elements, such as lancing or test elements, of a magazine are attached. The individual elements can have a foil that can serve as protection for the lancing or test element against the surroundings, and which can also serve as sterile protection. As a result, the magazine is not automatically enclosed by a housing or a foil, nor is it shielded against the surroundings by a foil or a membrane. Designs are also feasible in which the two magazines are stored together in a housing or a foil. In addition, the magazines can at least partially include sterile protection, e.g., in the form of a foil. In embodiments of the invention, at least the lancet tips have sterile protection.

The first holding structure with the at least one lancing element and the second holding structure with the at least one test element can be designed as a single component, or they can be composed of various elements. The holding structures can be composed of various materials, such as metal, ceramic, or plastic. In embodiments of the invention, the two holding structures are composed of a single part, which is made, e.g., of metal. In one embodiment, the holding structure is the magazine, since it does not include a further enclosure, such as a housing.

In the manufacture of a single-component lancing element magazine, it should be noted that the lancet tip should be suited to puncturing the skin of a body part. The lancet tip includes a distal region, which tapers into a sharp point. At least 2 lancets are stored in the magazine for lancing elements, but the first magazine can contain more than 100 lancets. In certain embodiments, there are up to 50 lancets in the first magazine. In embodiments of the invention, the second magazine also contains more than one test element. There can be more than 100 test elements in the second magazine. In certain embodiments, there are at least more than 50 test elements in the second magazine.

The magazines can have different shapes, such as stacked, disk-shaped, rows, and/or fan-folded. The two magazines do not have to have the same shape. In one embodiment, the two magazines are designed as circular disks. This circular-disk shape may be referred to as a lancet wheel in the case of the first magazine, and as a test element wheel in the case of the second magazine.

In embodiments of the invention wherein the first and second magazines have a substantially circular disk design, the wheels may include separately-located arms (lancet arm or test element arm), on the tips of which either a lancet tip or a detection area is located. In one embodiment, the wheel axes of the lancet wheel and the test element wheel are positioned perpendicularly to the opening plane of the opening. Due to the overlap of the wheels, and their orientation toward the opening inside the system, the lancet arm does not point toward the opening in this orientation. If the lancet tip is oriented parallel to the lancet arm, the lancet may be bent before use. As a result of this bending, the lancet tip is oriented orthogonally to the lancet arm, and the lancet tip points toward the opening and can therefore be moved toward the opening during the puncture procedure. The point at which the lancet tip is bent can be varied using a control element in the bending device. This allows the puncture depth to be varied, since the non-bent region of the lancet tip or the lancet arm can serve as the stop element during puncture of the skin. As an alternative, the lancet tip can be oriented orthogonally to the lancet arm directly or after the lancet wheel is manufactured, as is described with the related art in U.S. Pat. No. 4,794,926, which is hereby incorporated by reference in its entirety herein.

In alternative embodiments of the invention, it is also possible to use disks, which are moved in entirety toward the opening, in place of the above described lancet element wheel and test element wheel. It should be noted that generally, the smaller the mass of the disk, the smaller the drive necessary to drive the disk.

The lancet arms of the lancet wheel can be stamped and/or etched out of the circular structure. Other methods for manufacturing lancets known in the related art are also possible, however. The lancet tips can be formed in one step, either via stamping or etching. The lancet arm is resiliently connected with the lancet body so the lancet arm can be moved out of the circular plane of the lancet wheel. This deflection can take place below the plane of the lancet body or above the plane of the lancet body. This flexibility of the lancet arm can be attained using various methods. One possibility is to manufacture the lancet wheel out of very thin material (e.g., metal or plastic). Since the lancet wheel is thin, the lancet arms may bend easily. A further method for designing the lancet arm such that it is flexible relative to the lancet body is to provide an embossing at the transition point from the lancet arm to the lancet body. The embossing can be a tapering of the material, which can be created there, e.g., via stamping or etching.

In a further embodiment, the lancet can have a lancet tip which is suited for drawing up fluid. The suitability for drawing up fluid can be realized using various embodiments, such as forming a channel in the lancet tip. This channel can extend longitudinally along the entire lancet tip, or it can extend along just a part of the lancet tip. The channel may extend in the middle of the lancet tip and may extend beyond the length of the lancet tip. In one embodiment, this channel is formed through the entire material layer of the lancet tip. As an alternative, an absorbent material can be located on the proximal end of the lancet tip, with the aid of which fluid is drawn out of the wound. This lancet with fluid take-up capability is referred to below as a microsampler. The lancet wheel with the microsamplers may be located between the opening and the test element wheel. Since the lancet arm of the microsampler can be designed to be resilient, the blood collected in the channel can be transferred directly to the test element, which is located underneath the lancet wheel. To this end, the lancet arm is first moved toward the opening for puncture and blood drawing, and is then moved in the opposite direction toward the test element.

For hygienic use of the system, the lancet can be protected, at least in the tip region, by sterile protection. The lancet may be covered over the entire lancet body with a foil as the sterile protection. This sterile protection can be composed, e.g., of a polymer layer or a polymer cap, which is applied after production of the lancet structure. The sterile protection can also be composed of thin foils which enclose the lancet tip at the top and bottom, and which are pierced during the bending. These foils are advantageously held by a small frame, which is guided around the lancet tip. The sterile protection is pierced during the puncture procedure (e.g., through a part of the opening), or it is destroyed by the application of threshold force on the lancet tip by the lancet tip when it is bent, and the lancet tip is exposed. As an alternative, the sterile protection can be removed before the lancet is used. The sterile protection may be removed entirely. When the sterile protection is removed, the lancet tip should not be touched directly, to retain the sterility.

In one embodiment of the invention, desiccant is provided at various points in the housing and/or at least on one of the magazines, which ensures that the test elements are exposed to humidity that is lower than that of the ambient air. The stability of the test elements can be increased as a result. To hold the moisture in the housing relatively constant, the housing can have a seal against the surroundings, so that the magazine for the lancing elements and the magazine for the test elements are shielded against ambient humidity. As a result, a housing atmosphere may be created that has lower humidity than that of the ambient atmosphere. The housing opening may include a sealing mechanism which can be opened when used and then re-closed.

Given that a similar geometry can be selected for the two magazines, it is still possible to couple them with each other or to actuate them in a similar manner, yet to still control them individually. It is also possible, however, to couple the two magazines with each other such that they are moved simultaneously. For example, the two magazines can be installed in a housing, the entirety of which can be a disposable.

The blood can be tested for various components, as known in the related art. For example, the analysis can focus on blood components such as hematocrit, glucose, cholesterol, coagulation, iron, etc. Various methods can be used to perform the analysis. For example, electrochemical detection reactions can be used, or optical detection methods, such as reflectance, absorption, fluorescence, Raman spectroscopy, for example, or magnetic detection reactions. The test element may include at least one reagent layer, which is designed to change at least one property, in particular an optical and/or electrochemical property, upon contact with the at least one analyte to be detected. Typically, the fluid is brought in contact with a test system, and a reaction takes place between a test element and the fluid. Detection using an optical test element is based, e.g., on a color reaction between the fluid and the detection reagent. Examples of these reactions are described in U.S. Pat. Nos. 3,802,842, 4,061,468 and 4,490,465.

Mechanisms known from the related art, as described, e.g., in DE19604156, EP0565970, and U.S. Pat. Nos. 5,318,584 or 4,924,879, are used to drive the lancing element or the test element. An embodiment for the drive of the lancing element or the test element is the free motion of the element after force is transferred by the drive element, e.g., a push rod. In this embodiment, a pulse is transferred by the drive element to the lancing element or the test element, and the element is moved toward the housing opening without being driven further by the drive element. The motion of the lancet can be guided by additional elements on the housing.

As an alternative, the lancing element or the test element can be grasped by gripping elements and moved toward the opening.

The motion of the drive with respect to time can be varied. With guided puncture profiles of the lancet, for example, the motion toward the opening can take place more quickly than the motion away from the opening. This may be particularly preferred when the lancet is suited for drawing up fluid. The motion of the drive element can also be stopped during the puncture motion or during the exit motion away from the opening.

In a further embodiment, the drive unit can be suited to moving the lancing element or test element out of the position in the unused state, toward the opening, and in the opposite direction. In one embodiment, in which the holding structure is designed in the shape of a disk with radially outwardly or inwardly extending, resiliently supported arms, the spring force of the flexibly designed lancing element arm or the test element arm is used to tension the arm of the element in the direction opposite from the opening, and to accelerate the tensioned arm toward the opening, by releasing the tension, if necessary. This direction of motion of tensioning the arm can also be used to bring a lancing element in contact with a test element, e.g., to transfer fluid from the lancet tip or the microsampler to the test element.

In embodiments of the invention, the lancing element and test element are moved with a drive unit. The drive unit can have a different motion profile when the lancing element is driven than when the test element is driven. This can be ensured by an electronic control unit in the drive unit.

The change in the properties of the test element after sample is applied can be tracked, e.g., using optical detectors. These are conventional devices, such as photodiodes, CMOS devices, or CCD cameras, as are known in the related art.

BRIEF DESCRIPTION OF THE DRAWINGS

The above-mentioned and other features of this invention and the manner of obtaining them will become more apparent and the invention itself will be better understood by reference

Figure 1:
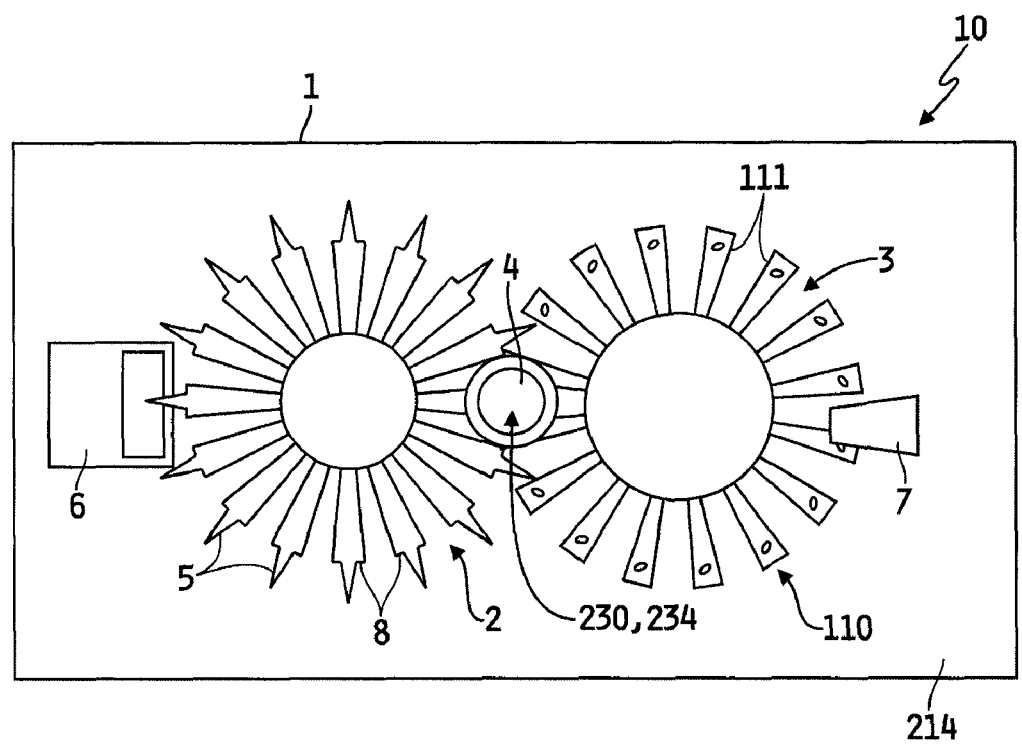
FIG. 1 is a top view of a schematic illustration of a system for analyzing a bodily fluid, with an opening, a magazine for lancing elements, and a magazine for test elements, which are positioned side-by-side.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates embodiments of the invention, and such exemplifications are not to be construed as limiting the scope of the invention in any manner.

DETAILED DESCRIPTION OF EMBODIMENTS OF THE INVENTION

For the purposes of promoting an understanding of the principles of the invention, reference will now be made to the embodiments illustrated in the drawings, which are described below. It will nevertheless be understood that no limitation of the scope of the invention is thereby intended. The invention includes any alterations and further modifications in the illustrated devices and described methods and further applications of the principles of the invention, which would normally occur to one skilled in the art to which the invention relates.

Figure 2:
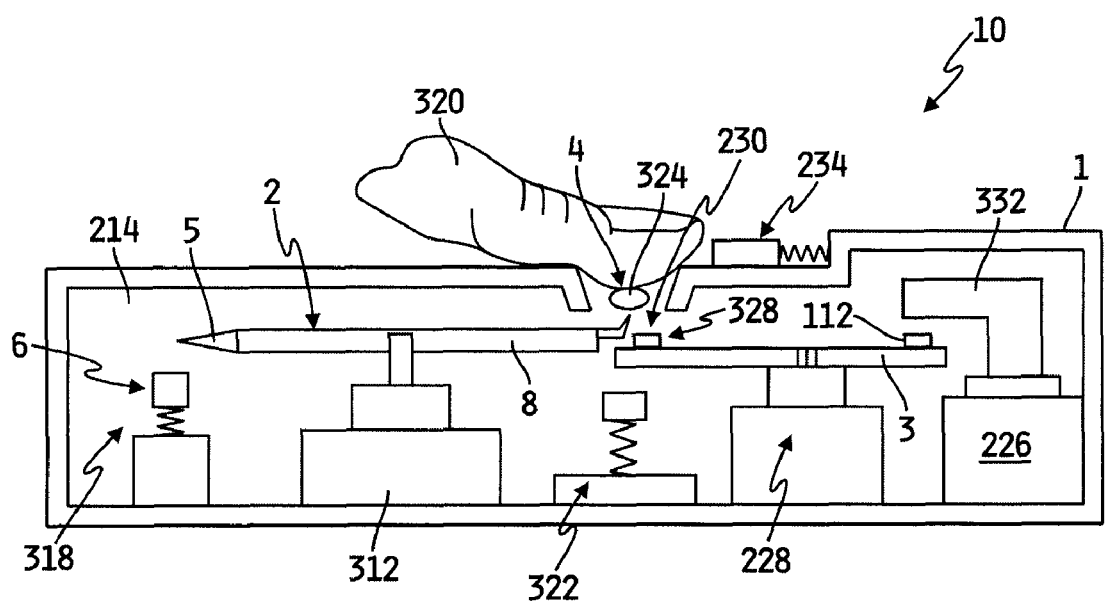
FIG. 2 is a side view of a schematic illustration of the system in FIG. 1 with bending device, drive, and detection unit.

In FIGS. 1 and 2, the system (10) and the mode of operation of the systems (10) for analyzing a bodily fluid are depicted schematically. FIG. 1 shows a top view of the system, and FIG. 2 shows a side view of the system. During operation, a lancet tip (5) to be used is first rotated in a bending station (6) in which a bending element (not shown here) is located. In this bending station (6), a spring mechanism (318) is used to bend the lancet (5) to be used upwardly by approx. 90° (in FIG. 2). Using the drive (312), the lancet wheel (2) is then rotated 180°, until the upwardly bent lancet tip (5) is located underneath the application opening (4) in the housing (1). In this exemplary embodiment, the application opening (4) is designed as a cone, and can be closed with a sealing element (234) before and after use. The sealing element (234) can be pushed to the side with the finger (320) of the patient, thereby exposing the application opening (4). The finger (320) simultaneously closes this application opening (4). By pressing the finger (320) on the application opening (4), the skin of the finger (320) forms a bulge which curves into the interior of the housing (1). When the portable measuring system is triggered, the lancet tip (5), which is bent upwardly and is located underneath the application opening (4), is accelerated via a spring mechanism (322) and perforates the skin of the finger (320) inside the application opening (4). A drop of blood (324) forms.

The test element wheel (3) designed in the shape of a circular disk in this exemplary embodiment according to FIGS. 1 and 2 is subdivided into circular disk sectors, the test element arms (111). Recesses (103) are located between these test element arms (111) (not shown in FIG. 2). When the lancet tip (5) punctures the skin, the test element wheel (3) is located in a configuration such that a recess (103) is located underneath the opening, so that the lancet arm (8) can be driven without restriction. Each of these test element arms (111) contains a test element (110) with a detection area (112). Each of these detection areas (112) includes a reagent layer (328) which, as described above, reacts to the presence and/or concentration of the analyte in the liquid sample (drop of blood (324)). In this exemplary embodiment according to FIGS. 1 and 2, this reagent layer (328) is, e.g., a reagent layer (328) which performs a color reaction in the presence of glucose, i.e., a reagent layer (328) that changes its color and/or fluorescence properties by reacting with glucose.

After the skin is perforated (as described above), the test element wheel (3) can be rotated using the drive (228) until the test element arm (111) can be bent upwardly briefly by the spring mechanism (322) toward the application opening (4). As a result, the drop of blood (324) is applied to the reagent layer (328) of the detection area (112), which is located in the application position (230), and the reaction described above can take place.

Subsequently, using the drive (228), the test element wheel (3) is rotated 180°, so that the detection area (112), to which the drop of blood (324) was applied, is located underneath an optical reader (332). This optical reader (332) carries out, e.g., a simple optical measurement or a fluorescence excitation measurement. The optical reader (332) is connected with the electronic evaluation device (226), which can include, e.g., a microprocessor, operating elements, displays, data memory, and the like.

It should be noted that in the depicted design, the lancet tip (5) and test element arm (8) can be driven with only one drive (322). The interior of the housing (1) with one opening (4) is protected by a seal (234) against environmental influences. When used, this seal (234) is slid to one side by the body part to be punctured, a finger (320) in this case, to expose the opening (4) of the housing (1) for use. The reagent layer (328) and the lancet tip (5) are thereby exposed to the atmosphere (214) inside the housing. A separate sealing of the individual detection areas (112) is not required but could be utilized. If so, the seal would have to be first removed from the individual reagent layers (328). This would require additional mechanical devices. A desiccant, for example, can be integrated in the test element wheel (3), which is designed as a circular disk in this case.

Figure 3:
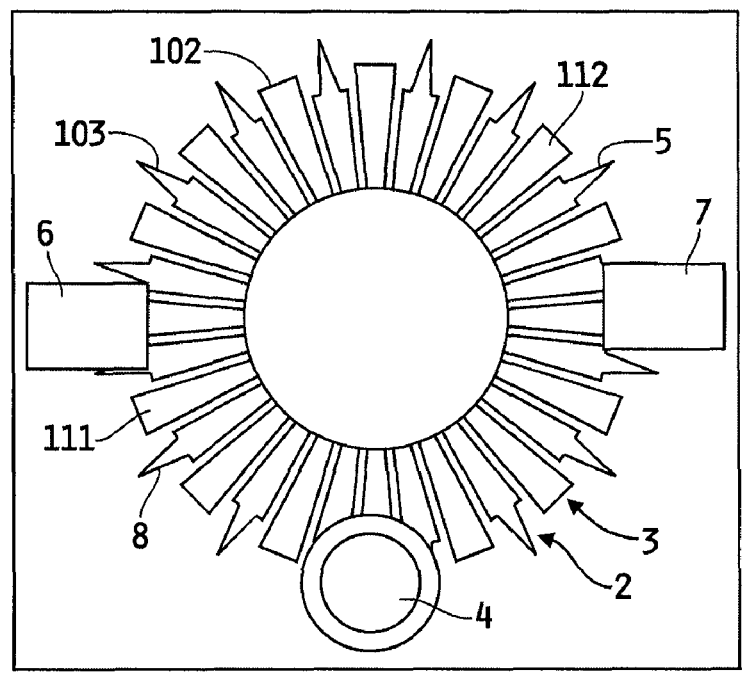
FIG. 3 is a schematic illustration of the two magazines for lancing elements and test elements, which are located one on top of the other.

A further possibility for positioning the two magazines, the lancet wheel (2) and the test element wheel (3), is shown in FIG. 3a. The two magazines are designed circular in shape and include recesses between their elements. The two circular magazines (2) and (3) may substantially or completely overlap. Due to the recesses (102) in the lancet wheel (2) and recesses (103) in the test element wheel (3), the lancet tips (5) and the detection areas (112) can be positioned such that they alternate, thereby preventing the elements from interfering with each other during use. This design of the magazines has the advantage that only one drive unit is required to index and/or drive the elements. Even when only one drive is used to index the magazine, it is possible to move the two magazines independently of each other. Since the magazines (2) and (3) can be designed to be very thin, it does not matter whether the lancet wheel (2) or the test element wheel (3) is closer to the opening. In the depicted overlapping geometry, it is possible to modify the system shown in FIG. 2 such that only one drive is required for the lancet arm (8) and for the test element arm (111). In the depicted embodiment, the opening (4) is not located between the bending point (6) and the detector (7).

Figure 4A:
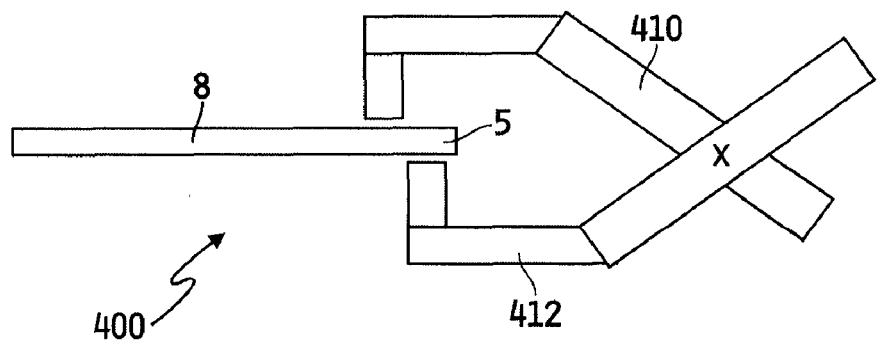
FIG. 4a is a schematic illustration of a device for bending the lancet tip, in the shape of tongs.

A device for bending the lancet tip (5) before puncture is shown in FIG. 4a. This is a tong-like structure (400), which includes two levers (410) and (412), which have different lengths. Lever (410) can be used to fix lancet arm (8) in position, while lever (412) exerts a threshold force in the direction of the other lever (410) on the lancet tip (5), to bend it out of the plane of the lancet arm (8). Depending on the extent of the force acting on the lancet tip (5), the lancet tip (5) can be bent by 90° out of the plane of the lancet arm (8).

Figure 4B:
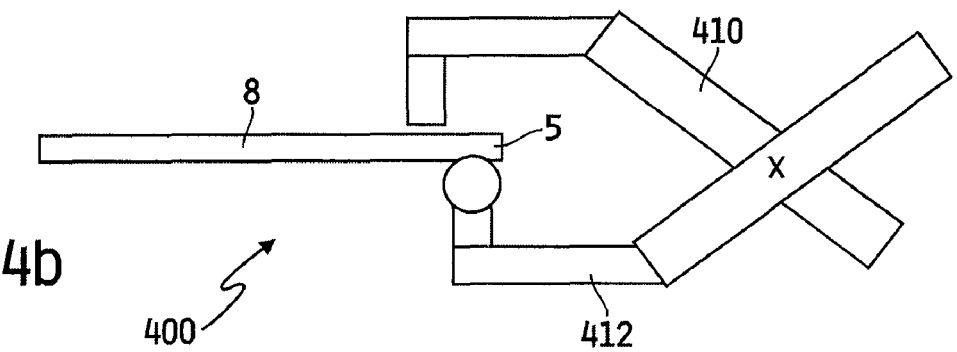
FIG. 4b is a schematic illustration of the device for bending the lancet tip, with a round tongs end.

A modification of this tong device in FIG. 4a is shown in FIG. 4b, in which the tip of at least one lever, e.g., lever (412) is designed round in shape, to prevent damage to the lancet tip (5) when it is bent. Further devices for bending thin sheets of metal are made known in the related art.

While the invention has been taught with specific reference to these embodiments, one skilled in the art will recognize that changes can be made in form and detail without departing from the spirit and scope of the invention. The described embodiments are to be considered, therefore, in all respects only as illustrative and not restrictive. As such, the scope of the invention is indicated by the following claims rather than by the description.

What is claimed is:

1. A system for analyzing a bodily fluid collected from a body part including:
   a housing having an opening;
   a first magazine located at least partially within the housing and including at least two lancing elements and a first recess disposed between the at least two lancing elements, the first magazine being moveable to align one of the at least two lancing elements with the opening to lance the body part; and
   a second magazine located at least partially within the housing and at least partially overlapping the first magazine, the second magazine including at least two test elements and a second recess disposed between the at least two test elements, the second magazine being moveable to align one of the at least two test elements with the opening to receive body fluid from the lanced body part;
   wherein the second recess exposes one of the at least two lancing elements to the opening when one of the at least two lancing elements is moved to align with the opening and the first recess exposes one of the at least two test elements to the opening when one of the at least two test elements is moved to align with the opening.

2. The system as recited in claim 1 wherein the one of the at least two lancing elements and the one of the at least two test elements are moved in succession toward the opening.

3. The system as recited in claim 1 further including a drive configured to incrementally move the first magazine.

4. The system as recited in claim 3 wherein the drive is configured to incrementally move the second magazine.

5. The system as recited in claim 1 further including a drive configured to move the one of the at least two lancing elements and the one of the at least two test elements toward the opening.

6. The system as recited in claim 5 wherein the drive is configured to move the other of the one of the at least two lancing elements and the one of the at least two test elements toward the opening.

7. The system as recited in claim 1 wherein at least one of the first magazine and the second magazine has a substantially circular profile.

8. The system as recited in claim 1 further including a resilient carrier wherein one of the lancing element and the test element is mounted on the resilient carrier in a manner allowing the one element to be deflected toward the opening.

9. The system as recited in claim 8 wherein the one element is mounted on the resilient carrier in a manner allowing the one element to be deflected away from the opening.

10. The system as recited in claim 1 wherein the lancing element is designed to draw fluid.

11. The system as recited in claim 10 wherein the one of the at least two lancing elements and the one of the at least two test elements are brought into contact with each other.

12. The system as recited in claim 1 further including a detection device.

13. The system as recited in claim 1 further including an evaluation device.

14. The system as recited in claim 1 further including a display.

15. The system as recited in claim 1 wherein the at least one lancing element includes a bend.

16. The system as recited in claim 1 wherein the one of the at least two lancing elements includes sterile protection.

17. The system as recited in claim 1 wherein the opening includes a press-down piece for placement of the body part on the opening.

18. The system as recited in claim 1 wherein the at least one recess exists before use of the system.

19. The system as recited in claim 1 wherein the at least one recess is defined without contact between the at least one lancing element and the at least one test element.

20. A system for analyzing a bodily fluid collected from a body part including:
   a housing having an opening;
   a first magazine located at least partially within the housing and including at least one lancing element and a first recess, the first magazine being moveable to align one of the at least one lancing element with the opening to position the lancing element for a puncturing procedure;
   a protection element configured to maintain at least a portion of one of the at least one lancing element in a sterile condition until the puncturing procedure, during which the portion of the one of the at least one lancing element is exposed to the atmosphere; and
   a second magazine located at least partially within the housing and at least partially overlapping the first magazine, the second magazine including at least one test element and a second recess, the second magazine being moveable to align one of the at least one test element with the opening;
   wherein the lancing element extends through the second recess during the puncturing procedure and the one of the at least one test element receives body fluid from the lanced body part through the first recess.

21. The system as recited in claim 20 wherein the protection element is formed from a polymer and encloses a tip of the lancing element.

22. The system as recited in claim 20 wherein the protection element includes a foil that encloses the portion of the lancing element, the foil being punctured during the puncturing procedure.

23. A system for analyzing a bodily fluid collected from a body part including:
   a housing having an opening;
   a first magazine including a plurality of adjacent lancing elements;
   a second magazine including a plurality of adjacent test elements;

wherein the first magazine is movable relative to the second magazine to align a lancing element of the first magazine between adjacent test elements of the second magazine to lance the body part through the opening and the second magazine is movable to align a test element of the second magazine between adjacent lancing elements of the first magazine to receive body fluid through the opening from the lanced body part.

24. A system for analyzing a bodily fluid collected from a body part including:

a housing having a housing opening;

a first magazine including a plurality of lancing elements separated from one another by a plurality of lancing element recesses;

a second magazine including a plurality of test elements separated from one another by a plurality of test element recesses;

wherein the first magazine is movable to align a lancing element of the plurality of lancing elements of the first magazine with an opening through a test element recess of the plurality of test element recesses of the second magazine to lance the body part and the second magazine is movable to align a test element of the plurality of test elements of the second magazine with an opening through a lancing element recess of the plurality of lancing element recesses of the first magazine to receive body fluid from the lanced body part.

* * * * *